United States Patent [19]
Smith

[11] Patent Number: 5,984,853
[45] Date of Patent: Nov. 16, 1999

[54] MINIATURIZED SOURCE OF IONIZING RADIATION AND METHOD OF DELIVERING SAME

[75] Inventor: Leif Smith, Uppsala, Sweden

[73] Assignee: Radi Medical Systems AB, Uppsala, Sweden

[21] Appl. No.: 08/805,296

[22] Filed: Feb. 25, 1997

[51] Int. Cl.⁶ .................. G21K 5/00; A61B 6/12
[52] U.S. Cl. .................................................. 600/1
[58] Field of Search .................. 600/1–8, 407, 600/427; 378/65, 64, 108, 116, 62, 145, 119, 121, 137, 138, 110, 112

[56] References Cited

U.S. PATENT DOCUMENTS 5,090,043  2/1992  Parker et al. .
5,442,678  8/1995  Dinsmore et al. .
5,729,583  3/1998  Tang et al. .

FOREIGN PATENT DOCUMENTS 0630 038 A1  12/1994  European Pat. Off. .
WO 97/07740  3/1997  WIPO .

OTHER PUBLICATIONS

Brodie, "Vacuum Microelectronic Devices", *Proceedings of the IEEE*, vol. 82(7):1006–1034, (1994).

*Primary Examiner*—Samuel Gilbert
*Attorney, Agent, or Firm*—Foley & Lardner

[57] ABSTRACT

A method and apparatus of creating a miniaturized source of radiation and delivering radiation to a location such as therapy location. The radiation source comprises a member made of a material emitting electrons when energy is supplied to the member. There is an electron retarding member disposed opposite the electron emitting member, and the electron retarding member is made of a material emitting ionizing radiation when electrons are retarded therein. The radiation source is further provided on an elongated member in the distal region thereof, and the elongated member is insertable into the body.

28 Claims, 5 Drawing Sheets

MINIATURIZED SOURCE OF IONIZING RADIATION AND METHOD OF DELIVERING SAME

BACKGROUND OF THE INVENTION

1. Field of the Invention

The invention relates to a method and apparatus for the use of radiation sources in therapy, and in particular to a miniaturized radiation source having the capability of being switched on and off at the operator's discretion.

2. Related Art

The manufacture of radiation devices has been developing during the last 30 years. The primary applications for these devices are in microelectronics, diods and transistors. However more recently, devices that generate radiation in the visible frequency region have been used for displays of the Flat Panel Display type, and this technology has become a separate research area for applications in the television field, etc. The primary effort has been to decrease the anode to cathode voltage, so that these devices can be used in general purpose electronic circuits. A more detailed description of this research can be found in an article entitled "Vacuum Microelectronic Devices", in *Proceedings of the IEEE*, Vol. 82 no. 7, July 1994.

In this article there are disclosed the principles and basic construction of micro field-emission sources. It is stated therein that it is necessary to have emission areas no larger than $10^{-2}$ cm$^2$ in order to obtain uniform field emission. Therefore, it is necessary to form the emitter in the shape of a needle with a tip having an end radius less than 1 μm. A specific design of the emitter is a metal cone, $10^{-4}$ cm tall with a tip radius of 30 nm. Also, there is disclosed the provision of an accelerating electrode (gate) spaced 60 from the tip.

In this application, these field emitting devices, among others, can be utilized to emit ionizing radiation with energies high enough to be used for medical therapy.

Radiation therapy is a well established method for treatment of several serious diseases, including cancer. Either alone or combined with other forms of therapy, the irradiation of human or animal tissue with ionizing radiation has proven to be very effective, and is used throughout the world and at several levels in health care organizations from specialized university clinics to regional and county levels. However, complications and side effects are often present. Ionizing radiation is biologically destructive in the sense that the structure of biomolecules is irreversibly changed, frequently leading to cellular disorganization, functional damage and even death. The result is also non-specific. A common problem is to limit the radiation exposure to areas of disease, to avoid destruction of healthy tissue.

Traditional radiation therapy makes use of radioactive nuclei, particle accelerators or high voltage generators to create radiation with such a high energy that it penetrates the patient's body. The radiation source is usually located outside the body, and means for collimating the radiation is used to concentrate it on the tissue where therapy is required. A difficult compromise is to maximize the therapeutic dose while minimizing the radiation exposure to healthy tissue.

In recent years, miniaturized radiation sources consisting of radioactive substances contained at the tip of a metal wire have been introduced. With such a localized radiation source it is possible to concentrate the dose to a small region. However, the use of radioactive substances is impractical for several reasons. First, the source must be properly shielded during introduction into the body to avoid exposure to healthy tissue. Second, all handling procedure must be carefully controlled to avoid exposure by mistake. Third, the dose and energy of radiation are not easily controlled.

SUMMARY OF THE INVENTION

The present invention provides an adequate solution to these problems. It has now been ascertained that the principle of field emission and thermionic emission is possible for use in medical procedures, namely for delivering radiation to a therapy location in a living body. One aspect of the invention comprises a miniaturized radiation source which is electronically controllable to generate exactly the required energy or wavelength of radiation. It can be switched on and off as desired. Furthermore, the delivered intensity and dose can be independently controlled, and the source can be manufactured with extremely small dimensions. For certain purposes it will have a volume of less than $10^{-3}$ mm$^3$, whereas for other purposes it may be as large as 1 cm$^3$.

Thus, in one aspect of the invention there is provided an apparatus for delivering radiation to a therapy location in a living body, comprising a miniaturized source of ionizing radiation, the radiation source ionizing radiation, the radiation source comprising a member made of a material emitting electrons when energy is supplied to the member, an electron retarding member disposed opposite the electron emitting member, the electron retarding member being made of a material emitting ionizing radiation when electrons are retarded therein, the radiation source being provided on an elongated member in the distal region thereof, and the elongated member being insertable into the body.

In another aspect of the invention there is provided a method of delivering radiation to a therapy location in a living body.

BRIEF DESCRIPTION OF THE DRAWINGS

The invention will be more fully understood from the following detailed description in conjunction with the drawings, wherein;

FIG. 4b is a cross-section taken along B—B in FIG. 4a;

DETAILED DESCRIPTION OF THE PREFERRED EMBODIMENTS

The basic physical principle behind the radiation source is well known from the literature of modern physics. When high energy electrons are retarded by nuclei having a large atomic weight, electromagnetic radiation is emitted. The primary radiation, denoted "bremsstrahlung", has a continuous spectrum with a peak corresponding to a given fraction of the electron energy. The emitted radiation can have an energy peak from a few electron volts (eV) to several million electron volts (MeV) depending on the energy of the incident electrons. In terms of wavelength, this corresponds to a range from ultraviolet light (10–4000 Å) via X-rays (0.1–100 Å) to gamma radiation (<0.10 Å). Thus, by varying the energy of the electrons, the wavelength peak can be displaced accordingly. In addition to bremsstrahlung, which basically has a continuous spectrum, absorption or emission peaks corresponding to atomic electron transition may be embedded in the spectrum, depending on the materials contained in the transmission medium.

Figure 1:
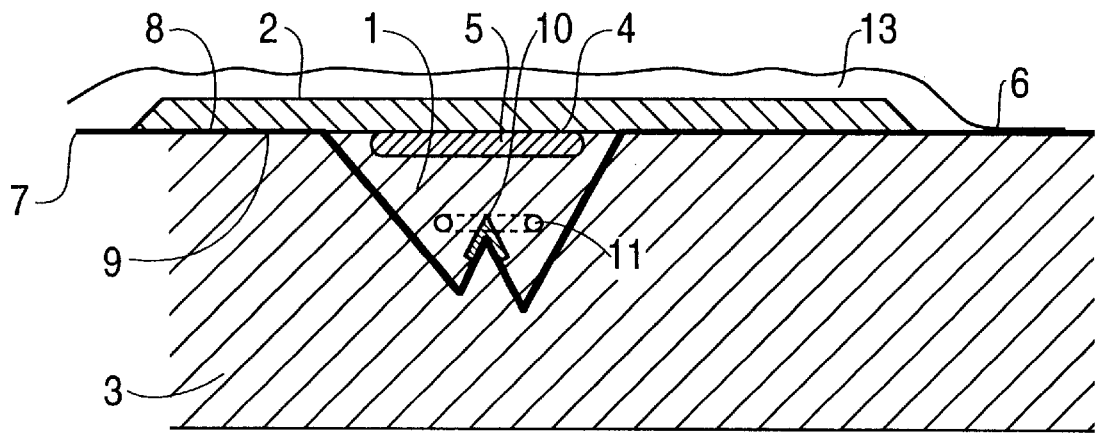
FIG. 1 shows a cross-section of the radiation source according to the invention, wherein the field emission principle is employed.
Figure 2:
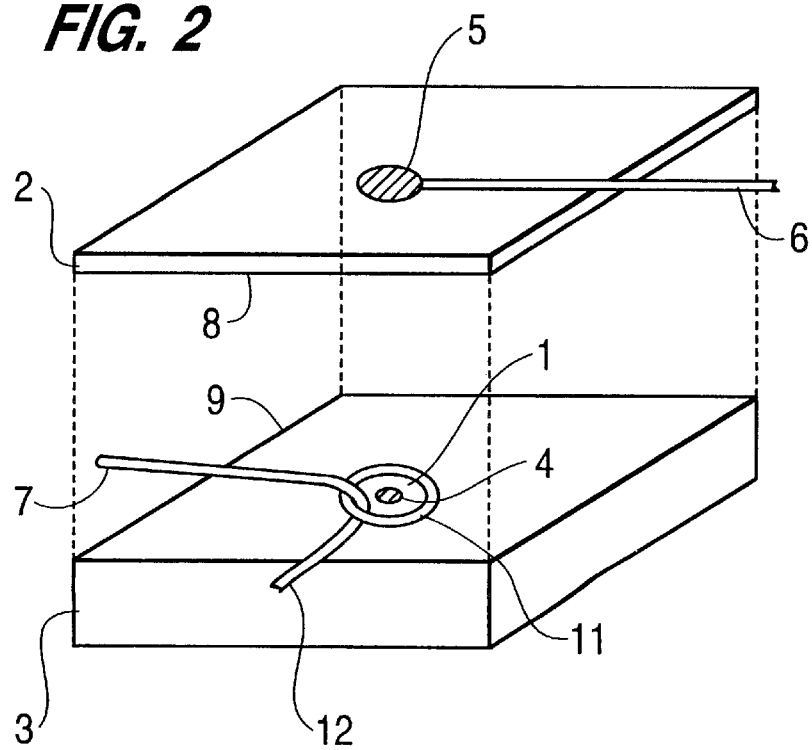
FIG. 2 shows an exploded perspective view of the radiation source according to the invention of FIG. 1.

The details of the radiation source and its function will be described with reference to FIGS. 1 and 2. Basically, the source is built up from two plates 2, 3 with a recessed region forming a microcavity 1 at one or several localities. An anode material 5 and a cathode 4 with extremely small dimensions, and having the form of a sharp tip 10 are located within this microcavity. The radius of curvature of the tip 10 of the cathode is preferably in the nanometer range. If a voltage is applied between the anode 5 and cathode 4, the electric field strength will be extremely high at the cathode. A positive voltage on the anode will cause electrons to be emitted from the cathode by the phenomenon known as field emission. Alternatively, the cathode may be heated to high temperatures, giving rise to thermal emission of electrons. This will be further discussed below with reference to FIG. 6. The electrons are accelerated by the electric field, until they are retarded by the impact at the anode. The anode 5 preferably consists of a metal having a high atomic weight, corresponding to an atomic number exceeding 50. In a preferred embodiment, the anode 5 is made of tungsten which is an endurable metal that can be deposited in the form of thin films either by physical or chemical deposition techniques. Other metals include cobalt, molybdenum and aluminium. The cathode preferably consists of a thin deposited film of a material having a low work function, i.e. the energy required for an electron to be emitted from the surface into the ambient. Materials with this property are oxides of metals from Groups I and II in the periodic table, including cesium, barium and magnesium.

The anode 5 and cathode 4, may be connected to a voltage source by electrically conducting leads 6, 7, which may, at least partly, be an integral part of the plates 2, 3. This can be achieved by deposition of stripes by evaporation, sputtering or chemical vapor deposition. Alternatively, if the plates 2, 3 are semiconductors, the leads 6, 7 may be doped regions according to well-known technology. In a preferred embodiment, a third electrode 11 is also present within the microcavity 1. This electrode 11 acts as a gate, controlling the electron current emitted toward the anode 5. The gate electrode has a separate lead 12, enabling a separate voltage source to be connected. According to the well-known theory of vacuum tubes, the anode current is controlled by the gate voltage. This will directly influence the intensity of the emitted radiation which is approximately proportional to the anode current. The emitted dose is simply the time integral of this intensity. By separate and independent control of the gate and anode voltages, it is thus possible to independently control the emitted dose and energy, respectively.

The leads 6, 7 and 12 must be properly isolated to avoid short circuit or current leakage. If the plate materials by themselves are not isolating themselves, passivating films may be necessary to ensure proper isolation. Furthermore, the lateral location of the leads is preferably chosen to minimize the electric field across material barriers. The voltage to the anode and cathode should preferably be in the kV range in order to obtain radiation of sufficient energy.

Figure 6:
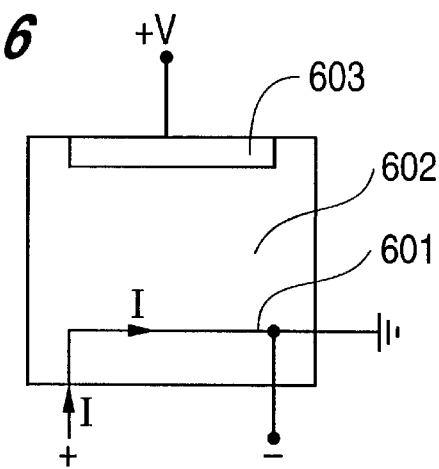
FIG. 6 shows schematically the radiation source according to the invention, wherein the thermionic emission principle is employed.

With reference to FIG. 6, there is schematically shown an implementation wherein the thermionic emission principle is employed. Through a thin wire 601 or filament disposed in a microcavity 602, such as the one disclosed above, a current I is passed. The temperature will be so high that electrons will be emitted and accelerated by an electronic voltage imposed across the filament 601 and an anode 603, also disposed in microcavity 602.

There are two principally different ways of fabricating the radiation source according to the invention. One way is to use two separate solid substrates and define the structures containing the cathode 4, the gate 11, with their leads 7 and 12, and the recess or microcavity 1 in one substrate. The anode 5 and its lead 6 are defined in the second substrates. Lithographic techniques according to well-known art are preferably used in defining these structures. Then finally the two substrates, corresponding to plates 2 and 3, are bonded together, using techniques such as solid-state bonding. If the bonding is performed in a vacuum, the microcavity 1 will remain evacuated, since the bonded seal is almost perfectly hermetic, provided that no organic materials are used. Absolute vacuum is not a necessity, but the density of gas molecules inside the microcavity must not be so high that the accelerating electrons are excessively impeded.

A requirement for successful bonding is that the bonded surfaces 8 and 9 are flat and smooth with a precision corresponding to a few atomic layers. A second requirement is that all structures are able to withstand a relatively high annealing temperature, approximately 600–1000° C., without damage. This first fabrication technique is basically known as bulk micromachining, in contrast to its alternative, surface micromachining. According to this, all structures are formed by depositions on one single substrate, again using lithography to define the two-dimensional pattern on the surface. The microcavity 1 is formed by first depositing a sacrificial layer which is etched away after the uppermost layers have been deposited. Closing the microcavity can be done by depositing a top layer, covering openings which are required for the etching of the sacrificial layer.

Both described methods of fabrication are feasible and lead to similar device performance. Indeed, from examining a final device, it may be difficult or even impossible to conclude which fabrication procedure has been used. An important characteristic of the proposed fabrication techniques is that the manufacturing cost per unit becomes very small when the source elements are fabricated in large numbers. This is due to the fact that batch fabrication with thousands of units per batch is feasible.

Figure 3A:
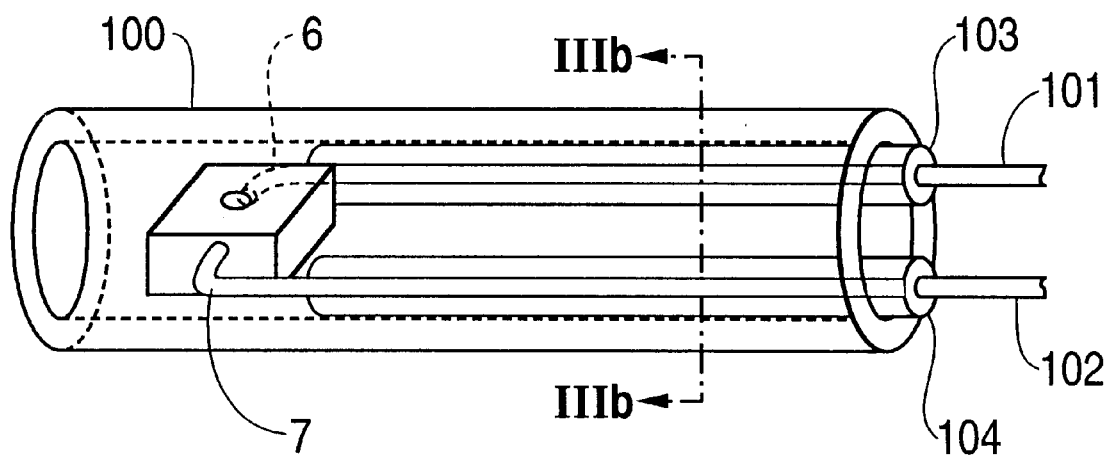
FIG. 3a illustrates an embodiment where the radiation source is mounted in a tube.
Figure 3B:
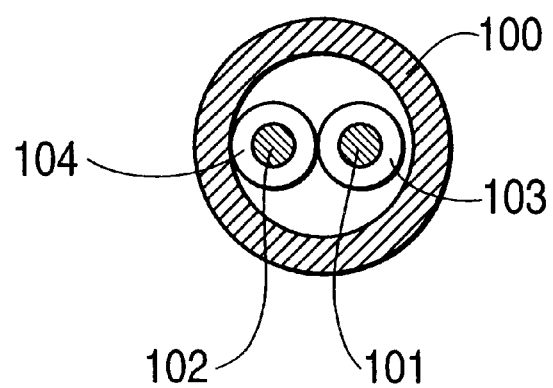
FIG. 3b is a cross-section of the tube of FIG. 3a, taken along B—B.

In FIG. 3 an embodiment is shown where the source and its leads 6, 7 are mounted inside a tubular element, such as its cannula 100, consisting of a material which is transparent to the emitted radiation.

Preferably, the tubular element (or the hollow portion where the source is mounted in the case of a needle), is made from elements having a low atomic number. As shown in the cross section A—A the leads 6, 7 are connected to wires 101, 102 having isolated mantles 103, 104. In a preferred embodiment, the outer diameter of the tubular element is smaller than 2 mm. The cannula is then sufficiently small to penetrate tissue in order to reach a certain location where radiation therapy is required.

Figure 4A:
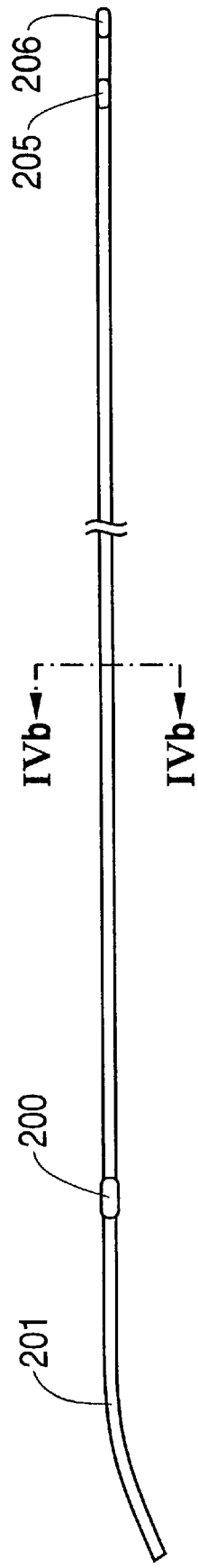
FIG. 4a illustrates an embodiment where the radiation source is mounted at the distal end of a guide wire.
Figure 4B:
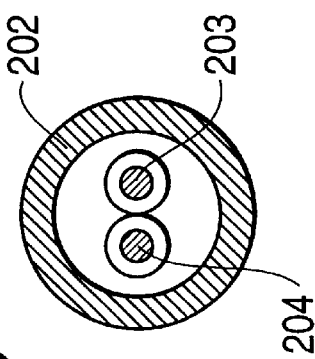

FIG. 4 shows a further embodiment where the source 200 is located near the distal end of a wire 201, having high bending flexibility in order to prevent organs and tissue from perforation or penetration by mistake. Instead, the wire 201 can be guided to the tissue where radiation therapy is required by insertion through a catheter which has previously been inserted in the tissue by well-known techniques. A cross section B—B of the wire 201 shows that it consists of a tubular member 202, and power transmitting leads 203, 204. The leads 203, 204 are proximally connectable to an external power source by connecting elements 205, 206. Geometrically, the connecting elements 205, 206 have a diameter approximately equal to the diameter of the wire to allow insertion of the wire into a catheter.

Figure 7B:
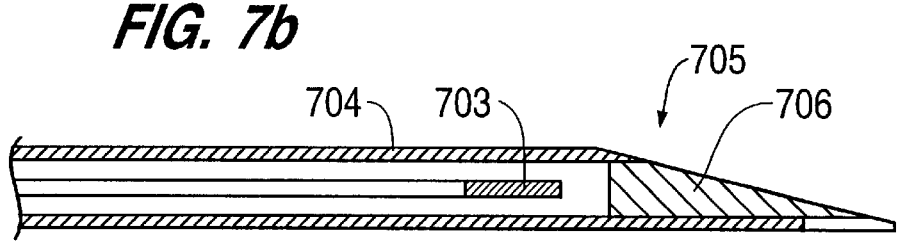
FIG. 7b illustrates a second alternative needle structure for accommodating a radiation source.
Figure 7A:
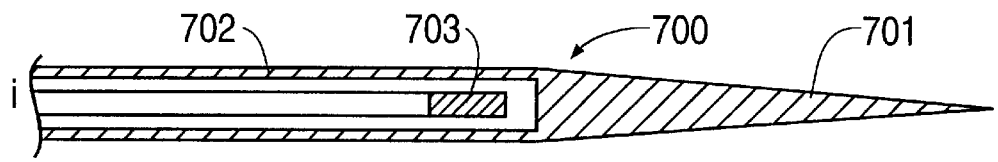
FIG. 7a illustrates an alternative needle structure for accommodating a radiation source.

Referring now to FIG. 7a and b, other vehicles for the radiation source are conceivable, e.g a needle 700 with a solid distal portion 701 having a sharp tip for the easy penetration of soft and hard tissue, and a hollow portion 702, proximal to the solid tip, wherein the radiation source 703 is mounted. In still another embodiment the radiation source may be mounted in a tube 704, the distal end of which, 705, has been bevelled to render it sharp enough for penetration purposes. The open end of the tube may be plugged at 706 so that the interior of the tube housing the source will not be soiled by tissue.

The power leads supplying power to the radiation source can either be electrical or fiberoptic leads, according to well-known technology. In the case of optical power transmission, it is necessary to convert the optical power into electrical voltage to provide voltage supply to the source. This may be done by providing optical energy through the fiberoptic leads and letting the light impinge onto a photodiode which converts the light into a voltage.

Figure 5:
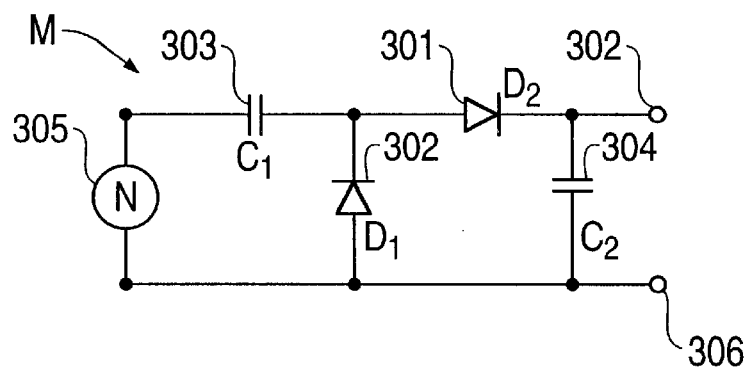
FIG. 5 shows an electronic circuit element, mediating voltage supply to the source.

FIG. 5 shows an electronic circuit element M capable of multiplying an input voltage 305 to its output terminals 307, 308 by a factor of approximately two. The circuit operates with two switching elements, for example diodes 301, 302, and two capacitors 303, 304. If two circuit elements as that shown in FIG. 5 are cascaded, the input voltage will be multiplied by a factor of approximately four. Even larger multiplication factors are possible by cascading more circuit elements of a similar type. The diodes 301, 302 may be replaced by other switching elements, such as transistors.

Figure 8A:
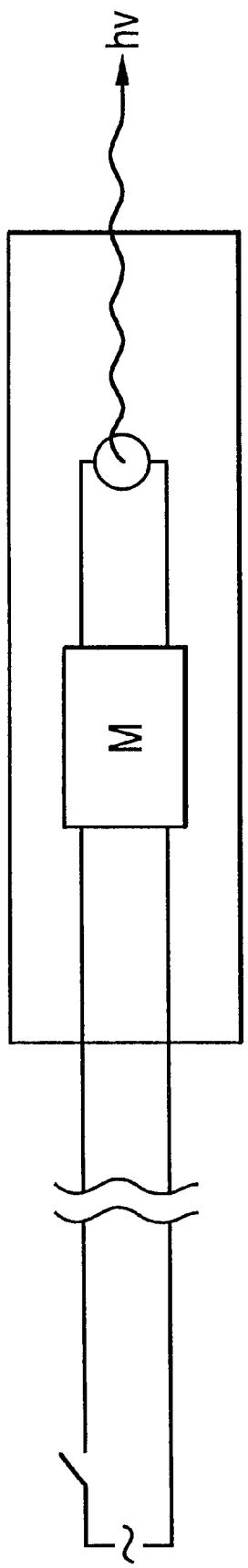
FIG. 8a is a schematic illustration of an integrated voltage multiplying circuit and a radiation source.
Figure 8B:
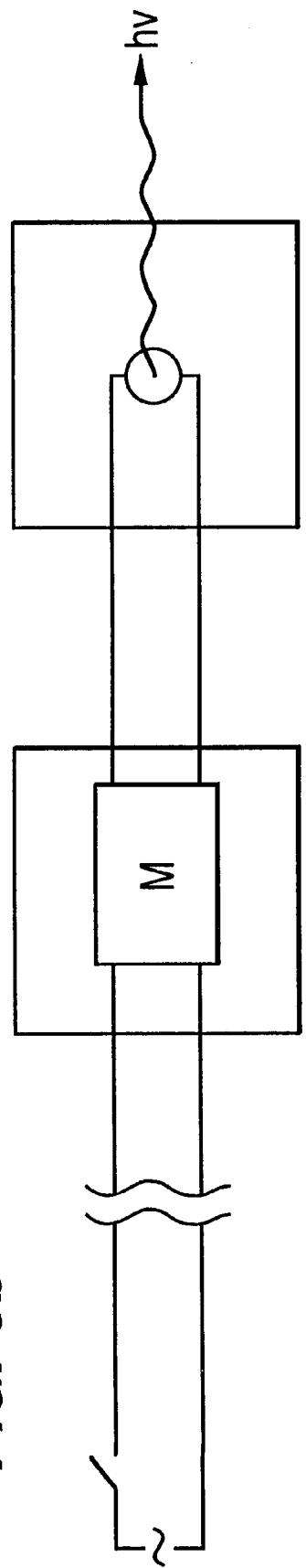
FIG. 8b is a schematic illustration of a voltage multiplying circuit and a radiation source disposed on separate chips adjacent each other.

Preferably, electronic circuitry M such as that shown in FIG. 5 may be integrated with one of the plates 2, 3 accommodating the source (schematically shown in FIG. 8a). Alternatively, the circuitry consists of a separate electronic chip located close to the source (schematically shown it FIG. 8b).

The high voltage generation may of course alternatively be disposed outside the body, e.g in the external power supply.

The method of providing a controlled dose of radiation is carried out as follows.

The physician localizes the region of interest, e.g. a tumor to be treated. Depending on the site and type of tissue, various vehicles for the radiation source may be employed, e.g. a needle for penetrating through soft tissue, or a guide wire possibly in combination with a catheter, or the insertion may be made through blood vessels or other body channels, such as intestines. When the radiation source has been correctly located inside the body, the radiation source is activated and the required dose is given. The device is switched off and the source is withdrawn from the patient. This procedure may be repeated frequently until the desired clinical result has been achieved.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. The method of invasively delivering radiation to a therapy location in a living body, comprising:
    a) forming a miniaturized source of ionizing radiation on a support comprising at least one plate member, including a pair of electrodes in the form of an anode and a cathode on the support;
    b) inserting the source into a living body and directing the source at the therapy location; and
    c) activating the source of ionizing radiation by selectively energizing and deenergizing the source so as to direct a highly accelerated electron emission from the cathode to the anode in the vicinity of the therapy location.

2. The method of claim 1, wherein the high electron emission is created by applying a positive voltage on the anode to cause electrons to be emitted from the cathode.

3. The method of claim 2, wherein the voltage is in kV range.

4. The method of claim 1, wherein the high electron emission is created by heating the cathode to a high temperature, giving rise to thermal emission of electrons toward the anode.

5. The method of claim 1, including, retarding the electron emission by impact at the anode.

6. The method of claim 1, including forming the anode of a metal selected from a group consisting of tungsten, molybdenum, cobalt and aluminium.

7. The method of claim 1, including forming the anode of a metal having an atomic number higher than 50.

8. The method of claim 7, including depositing the anode metal in the form of a thin film on a first plate member.

9. The method of claim 8, including forming the cathode with a thin deposited film of a material having a low work function on a second plate member.

10. The method of claim 9, including forming a miniature platform formed by the plate members.

11. The method of claim 10, including connecting the anode and cathode to a voltage source by deposition of metallic strips.

12. The method of claim 1 wherein the support includes a first plate and a second plate.

13. The method of claim 12, including forming the first and second plates of a semiconductor material and doping leads therein, and connecting the anode and cathode to a voltage source by doping leads onto the semiconductor.

14. The method of claim 12, including forming a microcavity in one of the first and second plates, and forming at least the cathode in the microcavity and the anode on the other plate.

15. The method of claim 12, including forming the microcavity by etching off a sacrificial layer between the first and second plates.

16. The method of claim 12, including adhesively bonding adjoining surfaces of the first and second plates.

17. The method of claim 12, including forming at least one of the first and second plates of simple crystalline silicone.

18. The method of claim 1, including forming the anode at least partly of a metal having an atomic number greater than 20.

19. The method of claim 1, including forming a third electrode in the form of a gate within the microcavity, controlling the electronic current emitted toward the anode.

20. The method of claim 1, including isolating the electrodes to prevent short circuits and current leakage.

21. The method of claim 1, including forming a sharp tip in the microcavity and forming the cathode on the tip.

22. The method of claim 1, including determining a desired radiation level and duration of radiation, and energizing the source to achieve the desired level and duration.

23. The method of claim 22, including deenergizing the source and withdrawing the source from the location.

24. The method of claim 22, including repeating the steps of inserting the source, deenergizing the source and withdrawing the source at selected time intervals.

25. The method of claim 1, including encompassing the source within a cannula element comprising material transparent to emitted radiation, penetrating tissue of the living body and directing the source in the cannula to the therapy location.

26. The method of claim 25, including connecting electrical leads to the anode and the cathode, connecting insulated wires to the leads and extending the wires through the cannula to a power source.

27. The method of claim 1, including mounting the source near a distal end of a wire.

28. The method of claim 27, including inserting a catheter into body tissue, and directing the source and wire through the catheter to the therapy location.

* * * * *